(12) United States Patent
Ohshida et al.

(10) Patent No.: US 6,169,197 B1
(45) Date of Patent: Jan. 2, 2001

(54) PROCESS FOR SEPARATION BETWEEN DIALKYL CARBONATE AND ALKYL CARBAMATE

(75) Inventors: Takuo Ohshida; Hiroaki Ohgi; Yoshihisa Arai; Masamichi Mizukami, all of Tsukuba (JP)

(73) Assignee: Mitsubishi Gas Chemical Company, Inc., Tokyo (JP)

( * ) Notice: Under 35 U.S.C. 154(b), the term of this patent shall be extended for 0 days.

(21) Appl. No.: 09/332,951

(22) Filed: Jun. 15, 1999

(30) Foreign Application Priority Data

Jun. 15, 1998 (JP) .................................................. 10-167187

(51) Int. Cl.⁷ ............................. C07C 68/08; C07C 68/06
(52) U.S. Cl. ......................... 558/274; 558/270; 558/271; 558/277
(58) Field of Search ..................................... 558/270, 271, 558/274, 277

(56) References Cited

FOREIGN PATENT DOCUMENTS

| 197 49 860 | 5/1998 | (DE) . |
| 041 622 | 12/1981 | (EP) . |
| 866 051 | 9/1998 | (EP) . |
| 57-26645 | 2/1982 | (JP) ............................. C07C/69/96 |

*Primary Examiner*—Michael G. Ambrose
(74) *Attorney, Agent, or Firm*—Sughrue, Mion, Zinn, Macpeak & Seas, PLLC (57) ABSTRACT

A process for separation between dialkyl carbonate and alkyl carbamate which comprises adding an aromatic hydroxy compound to a liquid comprising alkyl carbamate having an alkyl group having 3 to 6 carbon atoms and dialkyl carbonate having alkyl group having 3 to 6 carbon atoms to obtain a mixed liquid, and distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column.

24 Claims, 3 Drawing Sheets

FIG. 1
VAPOR-LIQUID EQUILIBRIUM OF
DIBUTYL CARBONATE / BUTYL CARBAMATE
(20 mmHg)

○ NO ADDITION
● ADDITION OF PHENOL

FIG. 2
VAPOR-LIQUID EQUILIBRIUM OF
DIBUTYL CARBONATE / BUTYL CARBAMATE
(20 mmHg)

○ NO ADDITION
● ADDITION OF p-CRESOL

_PROCESS FOR SEPARATION BETWEEN DIALKYL CARBONATE AND ALKYL CARBAMATE_

BACKGROUND OF THE INVENTION

1) Field of the Invention

The present invention relates to a process for separation between an organic carbonate and an organic carbamate and specifically, to an efficient process for separation between dialkyl carbonate and alkyl carbamate in a mixture containing dialkyl carbonate and alkyl carbamate. Alkyl carbonate having an alkyl group of 3 to 6 carbon atoms is readily synthesized from urea and useful as a raw material of other carbonates, particularly, aromatic carbonates including diphenyl carbonate.

2) Prior Art

Processes for producing dialkyl carbonate using urea or alkyl carbamate as a raw material have been already known. For example, U.S. Pat. No. 2,834,799 discloses to produce both alkyl carbamate and dialkyl carbonate from both urea and alcohol in the presence of at least stoichiometric amount of $BF_3$, but a proportion of dialkyl carbonate in the products is low and it fails to describe separation of dialkyl carbonate.

Japanese Patent Kokai (Laid-open) No. 57-26645 describes to produce dibutyl carbonate from both butyl carbamate and butanol in Example 14 and to separate dibutyl carbonate from the reaction liquid containing butyl carbamate by distillation under 17 mbar, but there is no description concerning formation of azeotrope. However, in fact, dibutyl carbonate forms an azeotrope with butyl carbamate in a wide pressure range, so that it is impossible to perform perfectly separation between dibutyl carbonate and butyl carbamate by conventional distillation processes.

When dialkyl carbonate is continuously produced from urea or alkyl carbamate, it is difficult to allow completely progress of the reaction. Therefore, in industrial production of dialkyl carbonate, it is necessary to separate dialkyl carbonate as the product from unreacted alkyl carbamate to recycle unreacted alkyl carbamate as the raw material.

However, dialkyl carbonate having an alkyl group of 3 to 6 carbon atoms, which can be easily synthesized from urea and is excellent as raw material of aromatic carbonates, has a boiling point close to that of alkyl carbamate. As described above, dibutyl carbonate forms an azeotrope with butyl carbamate, so that it is difficult to perform perfectly separation between dibutyl carbonate and butyl carbamate by conventional distillation processes.

The inventors, as a process to solve above-mentioned problems, suggested to use two distillation columns different in operation pressure to each other in Japanese Patent Application No.9-286913. Separation between dibutyl carbonate and butyl carbamate can be perfectly performed by application of above-mentioned process. However, in above-mentioned process, in order to make small an amount of an azeotropic mixture to be recycled from second distillation column to first distillation column and to increase the distillation efficiency, it is necessary to make large a pressure difference between two distillation columns. Thus, when an operating pressure of second distillation column was made higher, there occurred a problem that a distillation temperature was raised, so that butyl carbamate was partially decomposed.

Further, in order to produce continuously dialkyl carbonate, it is necessary to feed continuously urea as the raw material into a reactor. As methods for feeding a powder or particles such as urea to a reactor, usually, gravity feeders such as rotary feeder, table feeder, etc., thrust feeders such as belt feeder, vibrating feeder, shaking feeder, screw feeder, etc., air force feeder such as injection feeder, air slide, etc., or other feeder combined mechanisms thereof are used.

However, in the reaction for production of dialkyl carbonate, when urea was continuously fed to a reactor using a gravity feeder or a thrust feeder, there occurred a problem that urea was coagulated in the vicinity of discharge opening of a feeder and adhered to the discharge opening since urea contacted vapors containing ammonia and alkyl alcohol as main components in the reactor, so that urea could not be steadily fed. Further, when an air force feeder was used, contact of urea with vapors in the reactor could be avoided by use of a large amount of an air current. However, also in such case, there occurred a problem that vapors also in the reactor were released during exhaust of used air current from the reactor.

Japanese Patent Kokai (laid-open) Nos. 10-152455 and 10-152456 suggest a process which comprises producing dialkyl carbonate from urea and an alkyl alcohol having an alkyl group of 3 to 6 carbon atoms and then producing diaryl carbonate from dialkyl carbonate and an aromatic hydroxy compound. In this process, diaryl carbonate can be produced from low-priced urea and aromatic hydroxy compound by using again by-produced alkyl alcohol as a raw material of dialkyl carbonate. Thus, this process is excellent.

Japanese Patent Kokai (Laid-open) No. 10-259166 and Japanese Patent Application No. 9-221563 perform the reaction for production of dialkyl carbonate from urea in a high boiling point solvent, which makes it possible to perform the reaction under about atmospheric pressure. However, since ammonium carbamate was produced as a by-product in above-mentioned reaction, there occurred the same problem that total yield of intended dialkyl carbonate and alkyl carbamate as the intermediate product was about 80 to 90% and thus selectivity was low. Alkyl carbamate produced as the intermediate product can be used again as the raw material for production of dialkyl carbonate. However, also in case where alkyl carbamate was used as the raw material for production of dialkyl carbonate, there occurred the problem that selectivity was low.

SUMMARY OF THE INVENTION

An object of the present invention, in order to solve above-mentioned prior art problems, is to provide an efficient process for separation between dialkyl carbonate and alkyl carbamate in a mixture containing both dialkyl carbonate and alkyl carbamate, depressing decomposition of alkyl carbamate.

In order to solve above-mentioned prior art problems, as a result of detailed studies concerning vapor-liquid equilibrium of a mixture containing both dialkyl carbonate and alkyl carbamate in the presence of third component, the inventors have found that separation between dialkyl carbonate and alkyl carbamate becomes easy in the presence of an aromatic hydroxy compound such as phenol.

Thus, the inventors have found that when a liquid comprising dialkyl carbonate and alkyl carbamate is distilled in the presence of an aromatic hydroxy compound in a distillation column, separation between dialkyl carbonate and alkyl carbamate is easy without causing decomposition of alkyl carbamate and a mixture of dialkyl carbonate and the aromatic hydroxy compound from a top section of the distillation column and alkyl carbamate from a bottom section of the distillation column are obtained, respectively, and have accomplished the present invention.

That is, the present invention provides a process for separation between dialkyl carbonate and alkyl carbamate which comprises:

adding an aromatic hydroxy compound to a liquid comprising alkyl carbamate represented by the following general formula (1) and dialkyl carbonate represented by the following general formula (2) to obtain a mixed liquid, and distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column;

RO—CO—NH$_2$ (1)

RO—CO—OR (2)

wherein R is an alkyl group having 3 to 6 carbon atoms.

Further, the present invention provides a process for separation between dialkyl carbonate and alkyl carbamate which comprises:

separating a catalyst from a reaction mixture produced by reaction of an alkyl alcohol having 3 to 6 carbon atoms with urea and/or alkyl carbamate represented by the following general formula (1) in the presence of the catalyst, adding an aromatic hydroxy compound to thus obtained liquid comprising the alkyl carbamate and dialkyl carbonate represented by the following general formula (2) to obtain a mixed liquid, distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column;

RO—CO—NH$_2$ (1)

RO—CO—OR (2)

wherein R is an alkyl group having 3 to 6 carbon atoms.

The present invention provides also a process for producing diaryl carbonate which comprises:

(a) reacting an alkyl alcohol having 3 to 6 carbon atoms with urea and/or alkyl carbamate represented by the following general formula (1) in the presence of a catalyst, (b) separating the catalyst from a reaction mixture thus produced, (c) adding an aromatic hydroxy compound to thus obtained liquid comprising the alkyl carbamate and dialkyl carbonate represented by the following general formula (2) to obtain a mixed liquid, (d) distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column, (e) reacting the mixture comprising the dialkyl carbonate and the aromatic hydroxy compound from a top section of the distillation column, thereby producing alkyl aryl carbonate represented by the following general formula (3) and diaryl carbonate represented by the following general formula (4), and (f) producing diaryl carbonate represented by the following general formula (4) by allowing a disproportionation reaction of unreacted alkyl aryl carbonate produced in step (e)

RO—CO—NH$_2$ (1)

RO—CO—OR (2)

RO—CO—OAr (3)

ArO—CO—OAr (4)

wherein R is an alkyl group having 3 to 6 carbon atoms and Ar is non-substituted phenyl group or a phenyl group substituted by alkyl group, alkoxy group, aryl group, aryloxy group or halogen.

Moreover, the inventors have found that when dialkyl carbonate is continuously produced by reaction of urea with an alkyl alcohol having an alkyl group of 3 to 6 carbon atoms in a high boiling point solvent, urea can be continuously fed in a simple apparatus by feeding into a reactor in the state dispersed urea in the high boiling point solvent.

Further, the inventors have found that when dialkyl carbonate is produced from urea and an alkyl alcohol having an alkyl group of 3 to 6 carbon atoms, selectivity to dialkyl carbonate can be improved by setting a water amount to be introduced into a reactor to 3 mol % or below to total of urea and alkyl carbamate to be used as the raw materials.

DETAILED DESCRIPTION OF THE INVENTION

The present invention will be described in detail below.

The alkyl carbamate in the present invention is an alkyl carbamate represented by the following general formula (1) and the dialkyl carbonate in the present invention is represented by the following general formula (2);

RO—CO—NH$_2$ (1)

RO—CO—OR (2)

wherein R is an alkyl group of 3 to 6 carbon atoms.

The alkyl carbamate has the same alkyl group as that of dialkyl carbonate to be used.

Examples of dialkyl carbonate include dipropyl carbonate, dibutyl carbonate, dipentyl carbonate, dihexyl carbonate and each isomer thereof.

The aromatic hydroxy compound to be added in the present invention is phenol or phenol substituted with a lower alkyl group(s), a lower alkoxy group(s), a halogen(s), a nitro group(s), a cyano group(s), etc. Examples of the aromatic hydroxy compound include phenol, cresols including isomers thereof, xylenols including isomers thereof, ethyl phenols including isomers thereof, methoxyphenols including isomers thereof, fluorophenols including isomers thereof, chlorophenols including isomers thereof, nitrophenols including isomers thereof and cyanophenols including isomers thereof, among which, considering separation and aromatic carbonate to be obtained, phenol, cresols including isomers thereof and xylenols including isomers thereof are preferable.

As the distillation procedure in the present invention, batch wise or continuous process may be applied. In an industrial process, it is preferable to apply a continuous process. When a continuous process is applied, the aromatic hydroxy compound may be fed to the same step of a distillation column as that fed a liquid comprising dialkyl carbonate and alkyl carbamate, an optional step of a distillation column or plural steps of a distillation column.

As the distillation column, a packed column filled with a filler such as Sulzer Laboratory packing, Sulzer packing, Mellapak, Dixon packing, Raschig ring, etc, or plate columns used bubble cap trays, sieve trays, bubble trays, etc., may be used, In order to lower an operating pressure in a bottom section of a distillation column, a packed column with comparatively small differential pressure between a top section and a bottom section of distillation column is preferable.

The number of step of a distillation column to be required for separation between dialkyl carbonate and alkyl carbamate by distillation is altered depending upon an amount of the aromatic hydroxy compound to be added and reflux ratio. However, considering economy for both the amount of the aromatic hydroxy compound and the reflux ratio, the number of step of a distillation column is preferably 10 steps or above and more preferably 20 steps or above, and the reflux ratio is preferably 0.1 to 20 and more preferably 1 to 5, and the amount of the aromatic hydroxy compound to be added is preferably 0.1 to 10 times by mol and more preferably 0.5 to 5 times by mole to dialkyl carbonate.

Regarding the distillation temperature, in order to depress decomposition of alkyl carbamate, the bottom section temperature is preferably 160° C. or below and more preferably 140° C. or below.

It is preferable that the operating pressure distillation is set to maintain the bottom section temperature to 160° C. or below and more preferably 140° C. or below. Although the actual operating pressure is altered depending upon components of a liquid to be distilled, it is preferable to distill under a pressure of 100 mmHg or below.

The liquid comprising dialkyl carbonate and alkyl carbamate may be a liquid containing only two components of dialkyl carbonate and alkyl carbamate or a liquid containing above-mentioned two components and other components(s). For example, when dialkyl carbonate is produced from urea and alcohol, the reaction liquid contains dialkyl carbonate as the product, unreacted alcohol, alkyl carbamate as the intermediate product and a catalyst. When a solvent is used in the reaction, the reaction liquid further contains the solvent.

Although, when the process for separation of the present invention is applied to separation by continuous distillation using above-mentioned reaction liquid, the reaction liquid may be introduced without pretreatment, it is preferable to remove unreacted alcohol in advance. The catalyst may be removed in advance or may not be removed. In order to avoid unnecessary reaction, it is preferable to remove the catalyst in advance. When a solvent is used, it may be removed in advance. However, when a solvent having a higher boiling point than that of alkyl carbamate and dialkyl carbonate is used, it need not be removed.

In the present invention, dialkyl carbonate is produced by the following process. That is, dialkyl carbonate represented by the above-mentioned general formula (2) is produced by the reaction of an alkyl alcohol having an alkyl group of 3 to 6 carbon atoms with urea and/or alkyl carbamate represented by above-mentioned general formula (1) in the presence of a catalyst.

The catalyst is separated from the reaction mixture obtained by above-mentioned reaction. Then, the aromatic hydroxy compound is added to the mixture comprising alkyl carbamate represented by the general formula (1) and dialkyl carbonate represented by the general formula (2) thus separated the catalyst to separate dialkyl carbonate from alkyl carbamate.

The process for producing dialkyl carbonate in the present invention will be described in further detail.

The alkyl alcohol to be used as the raw material in the present invention is an alkyl alcohol of 3 to 6 carbon atoms. Examples of the alkyl alcohol include propanol, butanol, pentanol, hexanol and each isomer thereof.

In the present invention, the reaction of urea and/or alkyl carbamate with the alkyl alcohol is performed.

The alkyl carbamate of the present invention is an alkyl carbamate obtainable by the reaction of urea with the alkyl alcohol. In the production of dialkyl carbonate from urea and/or alkyl carbamate and the alkyl alcohol, it is possible to make the reaction of alkyl carbamate with the alkyl alcohol progress until alkyl carbamate disappears or it is possible also to stop the reaction of alkyl carbamate with alkyl alcohol before alkyl carbamate disappears and then to recover alkyl carbamate from the reaction liquid and use again it as the raw material.

In order to make rapidly the reaction progress, it is necessary to exhaust ammonia produced by the reaction outside the system. Therefore, it is preferable to attach a reflux condenser to the reactor and perform the reaction in the state refluxing the reaction mixture. When urea is used as the raw material, alkyl carbamate is initially produced. If a high temperature is applied in this stage, side reaction will occur. Preferable reaction temperature is 100 to 200° C. In the stage of producing dialkyl carbonate from alkyl carbamate, it is preferable that the reaction temperature is 160 to 260° C.

It is preferable that the reaction is performed in a high boiling point solvent having a boiling point of 180° C. on above. When a solvent having a boiling point less than 180° C. is used, conversion is lowered since the reaction temperature is low near atmospheric pressure. In order to secure preferable reaction temperature without using the high boiling point solvent, it is necessary to apply a pressure. It is possible to perform the reaction under about atmospheric pressure by using the high boiling point solvent. As preferable species of the high boiling point solvent, hydrocarbons and ethers are exemplified. Although the hydrocarbons may be aliphatic unsaturated hydrocarbons, saturated hydrocarbons or aromatic hydrocarbons with higher stability are preferable. As the ethers, aromatic ethers, aliphatic ethers and aromatic aliphatic ethers can be used.

Examples of preferable hydrocarbon solvent include undecane, dodecane, tridecane, tetradecane, pentadecane, hexadecane, heptadecane, octadecane, nonadecane, eicosane, tetramethyl pentadecane, dicyclohexyl, hexylbenzene, cyclohexylbenzene, heptylbenzene, octylbenzene, nonylbenzene, decylbenzene, undecylbenzene, diisopropylbenzene, triisopropylbenzene, pentamethylbenzene, methylnaphthalene, diphenylmethane, ethylbiphenyl, bibenzyl, in which each hydrocarbon includes isomers thereof.

Examples of preferable ethers include dihexyl ether, dioctyl ether, cyclododecyl methyl ether, diethylene glycol dimethyl ether, diethylene glycol dibutyl ether, triethylene glycol dimethyl ether, tetraethylene glycol dimethyl ether, butyl phenyl ether, benzyl phenyl ether, dibenzyl ether, diphenyl ether and ditolyl ether, in which each ether includes isomers thereof. When a melting point of a high boiling point solvent to be used is high, the melting point can be lowered by mixing above-mentioned solvent(s).

In the present invention, a proportion of the high boiling point solvent to urea to be fed is preferably about 1 to 10 mol to 1 mol of urea. Although alkyl alcohol as the raw material and a catalyst also are fed to a reactor, they can be fed together with the high boiling point solvent. The amount of alkyl alcohol to be fed is 1 to 3 mol to 1 mol of urea and the amount of catalyst to be fed is preferably 0.001 to 0.5 mol to 1 mol of urea, depending upon kinds of catalyst to be used.

Urea, alkyl carbamate, alkyl alcohol and the high boiling point solvent to be used in the reaction need be stored in a storage vessel under dried nitrogen or dried air so as not to increase water content or in a hermetically sealed state. In order to reduce water content, alkyl alcohol and the high boiling point solvent can be dried with a drying agent such as molecular sieves, magnesium sulfate anhydride, etc., or dried nitrogen or dried air is bubbled into them, and urea and alkyl carbamate also can be vacuum dried. When an amount of water contained in a charge liquid is large, selectivity to alkyl carbamate and dialkyl carbonate and yield of dialkyl carbonate are lowered. Therefore, it is preferable that an amount of water contained in a charge liquid is 3 mol % or below to total of urea and alkyl carbamate to be used in order to prevent lowering of selectivity to alkyl carbamate and dialkyl carbonate.

As the catalyst, known catalysts can be used. Japanese Patent Kokai (Laid-open) Nos.55-102542, 55-102543, 57-26645 and 57-175147 disclose many catalysts for the reaction, which can be used in the present invention. Among them, an oxide, a hydroxide, a halogenide, an inorganic salt, an organic salt, an alkoxide, an alkyl alkoxide and an alkyl substituted metal oxide of a metal selected from the group consisting of zinc, lead, copper, tin, titanium, gallium and indium have high activity for the reaction.

However, in order to make the reaction progress with high selectivity, it is important to select a catalyst to generate no water during the reaction among above-mentioned catalysts. Thus, it is preferable to use a halogenide, an inorganic salt, an organic salt, alkoxide or an alkyl alkoxide of above-mentioned metal. Examples of preferable catalyst include lead acetate, copper acetate, dibutyl dibutoxytin, tetrabutoxy titanium and gallium tributoxide. As tin type catalyst, $R'_2Sn(OR)_2$ or $R'_2SnO$ wherein R' is an alkyl group of 1 to 10 carbon atoms and R is the same alkyl group as that in the above-mentioned general formulas (1) and (2) is preferably used. Regarding the catalyst to generate water during the reaction, lowering of selectivity can be prevented by using again it after the reaction. For example, although dibutyltin oxide is a catalyst with high activity for the reaction, selectivity is lowered since water is generated during the reaction. Therefore, when dibutyltin alkoxide formed by the reaction of dibutyltin oxide with alkyl alcohol is used as the catalyst or a catalyst used for the reaction is used again, selectivity to alkyl carbamate and dialkyl carbonate and yield of dialkyl carbonate are improved.

The urea to be fed in the present invention may be urea for reagent, urea for industry, urea for agriculture or coated urea. When bulky urea is used, it is necessary to pulverize it in advance in order to prevent blockage of pipe, valve, pump, etc., to be used for feeding.

Figure 3:
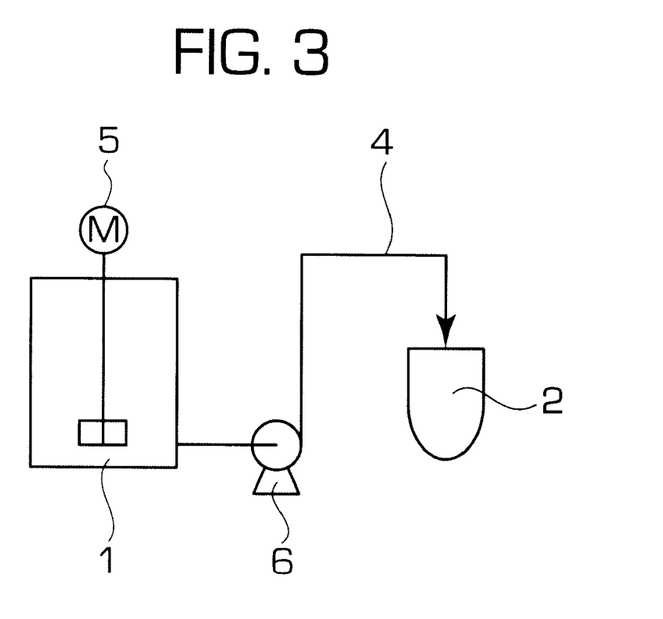
FIG. 3 is a schematic illustration showing one example of a feeding apparatus of urea in the present invention.
Figure 4:
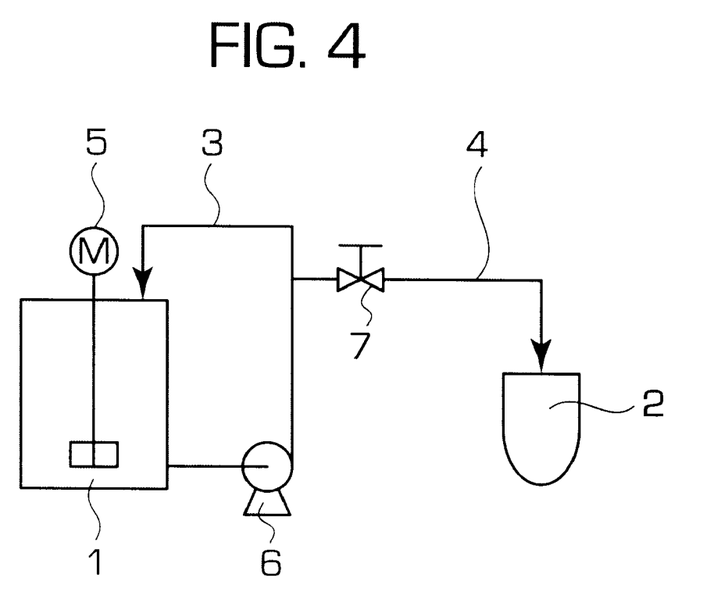
FIG. 4 is a schematic illustration showing one example of a feeding apparatus of urea in the present invention.

The present invention has a feature that urea to be used as the raw material is fed in the state dispersed in above-mentioned high boiling point solvent. Urea can be fed in the state dispersed in the high boiling point solvent, for example as shown in FIG. 3, by providing with a mixing vessel. Urea and the high boiling point solvent can be charged in batch wise or continuously into the mixing vessel to feed urea into a reactor in the state dispersed in the high boiling solvent. It is preferable that the mixing vessel is provided with a baffle plate in order to improve efficiency of stirring. They can be fed into a reactor with a conventional pump such as slurry pump. When a linear velocity of feeding in a feeding pipe is small, urea is settled depending on particle sizes of urea and further blockage occurs. In such case, as shown in FIG. 4, settlement of urea and blockage can be prevented by feeding a portion of a feed liquid while circulating it between a mixing vessel and a pump.

In the present invention, in order to exhaust ammonia by-produced in the reactor outside the system, the reactor is provided with a reflux condenser and the reaction is performed in the state refluxing the reaction mixture.

The mixture of dialkyl carbonate and the aromatic hydroxy compound obtained from a top section of a distillation column in the process of the present invention can be used as raw materials for production of the corresponding aromatic carbonate or pure dialkyl carbonate can be readily obtained from the above-mentioned mixture by further distillation When the mixture of dialkyl carbonate and the aromatic hydroxy compound is used as raw materials for production of the corresponding aromatic carbonate, it is preferable that dialkyl carbonate is mixed in advance with the aromatic hydroxy compound of 2 times by mole to dialkyl carbonate and then the mixture thus obtained is fed to a distillation column and distillation is performed so as to maintain a molar ratio of dialkyl carbonate to aromatic hydroxy compound in the top section liquid of the distillation column to 1:2. Further, where distillation is performed in a molar ratio of dialkyl carbonate to aromatic hydroxy compound of about 1:2, after distillation, either one of dialkyl carbonate or aromatic hydroxy compound can be also added to the top section liquid thus produced to adjust a proportion of both components to a proportion to be required as raw materials for production of the corresponding aromatic carbonate.

As a catalyst for production of alkyl aryl carbonate or dialkyl carbonate, an oxide, an alkoxide, an aryloxide or an alkyl substituted oxide of a metal selected from the group consisting of tin and titanium or a mixture containing at least member selected from said compounds are exemplified.

PREFERRED EMBODIMENTS OF THE INVENTION

Some of the preferred embodiments of the present invention will be described in detail below, referring to Examples, which are not intended to limit the scope of the present invention.

Butanol and diphenyl ether dried with molecular sieves and vacuum dried urea were used below.

REFERENCE EXAMPLE
[Measurement of vapor-liquid equilibrium]

Figure 1:
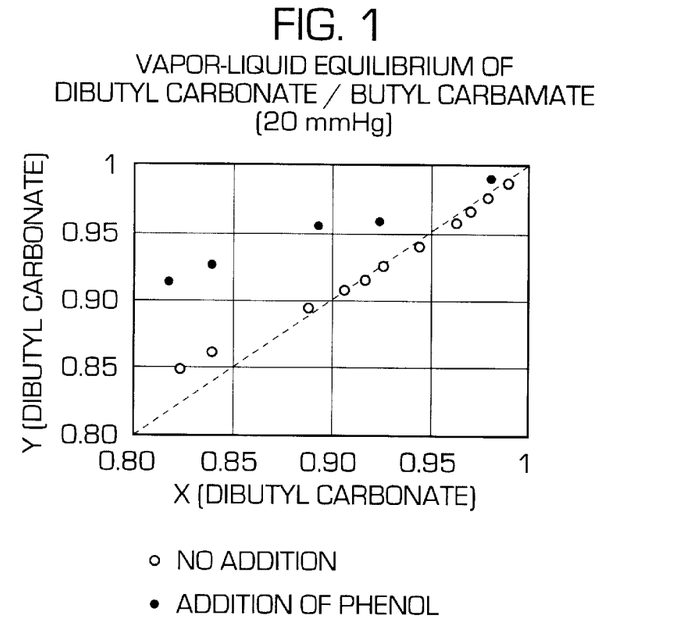
FIG. 1 is a diagram showing vapor-liquid equilibrium of dibutyl carbonate/butyl carbamate in the addition of phenol.
Figure 2:
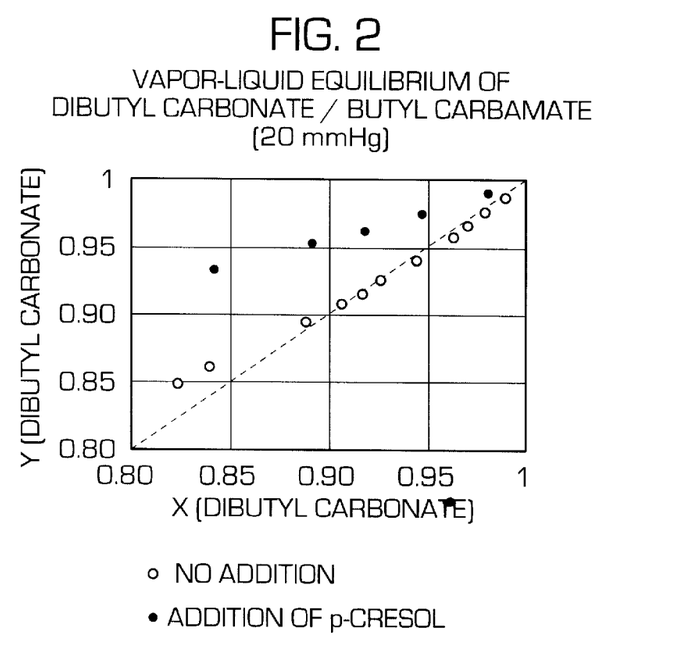
FIG. 2 is a diagram showing vapor-liquid equilibrium of dibutyl carbonate/butyl carbamate in the addition of p-cresol.

Vapor-liquid equilibrium between dibutyl carbonate and butyl carbamate in case of molar fraction 0.5 of aromatic hydroxy compound in three components system of dibutyl carbonate, butyl carbamate and aromatic hydroxy compound was measured with an Othmer type vapor-liquid equilibrium measuring apparatus. Each graph of measured result of vapor-liquid equilibrium under 20 mmHg in each case where each of phenol and p-cresol was used, was shown in FIGS. 1 and 2. In both cases, azeotrope disappeared by adding phenol or p-cresol. This means that separation between dibutyl carbonate and butyl carbamate by distillation becomes easy.

EXAMPLE 1

A liquid containing 42.6% by weight (hereinafter, "wt %") of dibutyl carbonate, 11.4 wt % of butyl carbamate and 46.0 wt % of phenol was fed at the rate of 300 g/hr at 100° C. to a center portion of a distillation column made from glass provided with a vacuum jacket (filled Sulzer Labopacking, inner diameter 50 mmφ, height of filling portion: concentration portion 550 mm, recovery portion 550 mm) and the continuous distillation was performed under a top section pressure of 20 mmHg in the distillation column. The distillation column was operated in a reflux ratio of 3 and adjusted to distill out 265 g/hr of a distillate from the top section and thus steady state was maintained. In the distillation, a liquid containing 48.2 wt % of dibutyl carbonate and 51.8 wt % of phenol was obtained as a distillate of the top section. Butyl carbamate content in the liquid thus obtained was below 0.05 wt %. A liquid containing 98.0 wt % of butyl carbamate and 2.0 wt % of phenol was obtained at the rate of 35 g/hr from the bottom section. Dibutyl carbonate content in the liquid thus obtained was below 0.05 wt %. In this distillation, the top section temperature was 94° C. and the bottom section temperature was 118° C.

A liquid containing 48.2 wt % of dibutyl carbonate and 51.8 wt % of phenol obtained from the top section of the distillation column was fed at the rate of 100 g/hr at 50° C. to a distillation column made from glass provided with a vacuum jacket (filled Sulzer Labopacking, inner diameter 50 mmφ, height of filling portion : concentration portion 550 mm, recovery portion 1100 mm) and then continuous distillation was performed under a top section pressure of 20 mmHg. The distillation column was operated in a reflux ratio of 12 and adjusted to distill out 53 g/hr of a distillate from the top section and thus steady state was maintained. In the distillation, about pure dibutyl carbonate containing 99.0 wt % of dibutyl carbonate was obtained in the rate of 47 g/hr from the bottom section. A liquid containing 96.7 wt % of phenol was obtained at the rate of 53 g/hr as the top section distillate. In this distillation, the top section temperature was 87° C. and the bottom section temperature was 110° C.

EXAMPLE 2

A liquid (A) comprising dibutyl carbonate and butyl carbamate was obtained by the reaction of urea with butanol in the presence of dibutyltin oxide catalyst in diphenyl ether solvent. The liquid (A) thus obtained was distilled in a distillation column. A liquid containing diphenyl ether and the catalyst as main components was removed from the bottom section. The liquid (A) was again distilled. A liquid containing butanol as main component from top section was removed. Thus, a liquid containing 82.3 wt % of dibutyl carbonate, 17.3 wt % of butyl carbamate and 0.4 wt % of diphenyl ether were obtained. Phenol was added to the liquid thus obtained to prepare a liquid (B) containing 43.4 wt % of dibutyl carbonate, 9.1 wt % of butyl carbamate, 0.2 wt % diphenyl ether and 47.3 wt % of phenol. Thus, the liquid (B) was used as a feed liquid.

The feed liquid was fed at the rate of 400 g/hr at 98° C. to a center portion of a distillation column made from glass, provided with a vacuum jacket (filled Sulzer Labopacking, inner diameter 50 mmφ, height of filling portion: concentration portion 550 mm, recovery portion 550 mm) and then continuous distillation was performed under a top section pressure of 20 mmHg in the distillation column. The distillation column was operated in a reflux ratio of 2 and adjusted to distill out 362 g/hr of a distillate from the top section and thus steady state was maintained. In the distillation, a liquid containing 48.0 wt % of dibutyl carbonate, 51.9 wt % of phenol and 0.1 wt % of butyl carbamate was obtained as a distillate of the top section. A liquid containing 95.4 wt % of butyl carbamate, 2.5 wt % of phenol and 2.1 wt % of diphenyl ether was obtained at the rate of 37 g/hr from the bottom section. Dibutyl carbonate content in the liquid was below 0.05 wt %. In this distillation, the top section temperature was 94° C. and the bottom section temperature was 118° C.

1795 g of the top section liquid obtained above containing 862 g of dibutyl carbonate, 932 g of phenol and 1 g of butyl carbamate and 16.8 g of titanium tetrabutoxide were charged into a round bottom flask of capacity 5 L in which a distillation column made from glass provided with a vacuum jacket (filled Sulzer Labopacking, inner diameter 50mmφ, height of filling portion 1100 mm) was connected to an upper portion thereof. The contents in the flask were heated with a mantle heater while stirring at 300 rpm with a mechanical stirrer. When the bottom section temperature became 191° C., reflux was started. All reflux was performed for 10 minutes after starting of reflux and then distillation-out was started in a reflux ratio of 30. The starting time of distillation-out was regarded as starting of the reaction. The yield (mol %) of butyl phenyl carbonate based on charged dibutyl carbonate was analyzed by gas chromatography. The yield was 12.3% in the reaction for 30 min., 18.6% in the reaction for 60 min., 22.5% in the reaction for 90 min., 27.4% in the reaction for 120 min., and 30.0% in the reaction for 150 min. The amount of distilled-out liquid was 131 g and the distilled-out liquid contained 128 g of butanol and 3 g of phenol. The bottom section temperature was 192° C. at the starting time of distillation-out and 197° C. after 150 minutes of starting of the reaction.

After 150 minutes of starting of the reaction, the reflux ratio was set to 0.2 and unreacted phenol and dibutyl carbonate were mainly distilled out in a reflux ratio of 0.2 by lowering gradually the reaction pressure from atmospheric pressure to 450 mmHg. After 40 minutes, unreacted phenol and dibutyl carbonate were almost distilled out. At this time, the bottom section temperature was 205° C. Then, dibutyl carbonate due to disproportionation was mainly distilled out by further lowering gradually the reaction pressure to 100 mmHg. After 2 hours of setting the reflux ratio to 0.2, the reaction was completed. At this time, the reaction liquid was analyzed. At this time, the bottom section temperature was 207° C. The distilled-out liquid contained 668 g of dibutyl carbonate, 774 g of phenol and 18 g of butanol. The bottom liquid was further distilled in order to remove the catalyst, whereby 133 g of diphenyl carbonate was obtained as the distillate.

According to the process of the present invention, it is possible to lower an operating pressure of a distillation column, so that it becomes possible to separate dialkyl carbonate from a liquid containing dialkyl carbonate and alkyl carbamate without causing decomposition alkyl carbamate. The mixture of dialkyl carbonate and aromatic hydroxy compound obtained in the process for separation of the present invention can be used as a raw material for production of the corresponding aromatic carbonate. Thus, the process for separation of the present invention is very excellent.

EXAMPLE 3

510 g (8.49 mol) of urea, 5782 g (34.0 mol) of diphenyl ether, 656 g (8.85 mol) of n-butanol and 78.2 g (0.314 mol) of dibutytin oxide were charged into mixing vessel 1 of 10 L provided with a baffle plate shown in FIG. 3. The contents in mixing vessel 1 were stirred with mechanical stirrer 5 to disperse uniformly urea. The mixture thus obtained was intermittently fed from the bottom section of mixing vessel 1 to reactor 2 of 1 L with the apparatus shown in FIG. 3 by roller pump 6 with an intermittent timer via feeding pipe 4 while uniformly dispersing urea in mixing vessel 1. The feeding rate was set to 500 g/hr by repeating OFF for 90 seconds and ON for 3.5 seconds with the intermittent timer. The reaction was performed in reactor 2 provided with a double tube type condenser at a reaction liquid temperature of 180° C. for 8 hours while passing hot water of 60° C. through the condenser and stirring at 600 rpm with a mechanical stirrer. Urea could be steadily fed during continuous reaction for 8 hours.

EXAMPLE 4

510 g of urea for industry, produced by Mitsui Chemical Co., Ltd., Japan, 5782 g (34.0 mol) of diphenyl ether, 656 g (8.85 mol) of n-butanol, 78.2 g (0.314 mol) of dibutyltin oxide were charged into mixing vessel 1 provided with a baffle plate of 10 L shown in FIG. 4. The contents in mixing vessel 1 were stirred with mechanical stirrer 5 to disperse uniformly urea. The slurry in mixing vessel 1 was circulated via circulating pipe 3 by centrifugal pump 6 with the apparatus shown in FIG. 4 while uniformly dispersing urea in mixing vessel 1. Further, the mixture thus obtained was intermittently fed into reactor 2 of 1 L via feeding pipe 4 branched from circulating pipe 3, provided with diaphragm valve 7 with a in an intermittent timer. The feeding rate was set to 500 g/hr by repeating closing for 100 seconds and opening for 0.5 second with the intermittent timer. The reaction was performed in reactor 2 provided with a double tube type condenser at a reaction liquid temperature of 180° C. for 8 hours while passing hot water of 60° C. through the condenser and stirring at 600 rpm with a mechanical stirrer. Urea could be steadily fed during continuous reaction for 8 hours.

EXAMPLE 5

Urea was fed in the same manner and apparatus as in Example 4 except that 36 g/hr of urea for industry, produced by Mitsui Chemical Co., Ltd., Japan, with a screw feeder, 411 g/hr of diphenyl ether, 47 g/hr of n-butanol and 5.6 g/hr of dibutyltin oxide was continuously supplemented into mixing vessel 1. Urea could be steadily fed during continuous reaction for 8 hours.

COMPARATIVE EXAMPLE 1

64.8 g (1.08 mol) of urea for industry, produced by Mitsui Chemical Co., Ltd., 740 g (4.35 mol) of diphenyl ether, 84.6 g (1.14 mol) of n-butanol and 10.1 g (40.6 mmol) of dibutyltin oxide were charged into reactor 2 of 1 L, provided with a double tube type condenser. The contents in reactor 2 were heated to 180° C. with stirring at 600 rpm with a mechanical stirrer while passing hot water of 60° C. through the condenser. It was attempted to feed further urea for industry, produced by Mitsui Chemical Co., Ltd., to a reactor 2 at the rate of 36 g/hr with a screw feeder while continuously feeding 411 g/hr of diphenyl ether, 47 g/hr of n-butanol and 5.6 g/hr of dibutyltin oxide into reactor 2, but urea was contacted reaction vapors to coagulate in a discharge opening of the screw feeder, so that urea could not be steadily fed.

When dialkyl carbonate is continuously produced from urea and alkyl alcohol in the process of the present invention, urea can be steadily fed with a simple apparatus.

EXAMPLE 6

Dibutyltin oxide was heated to 190° C. in diphenyl ether and then butanol was dropwise added thereto. Water produced by the reaction and excess butanol were distilled out, whereby a diphenyl ether solution of dibutyltin dibutoxide was prepared.

Figure 5:
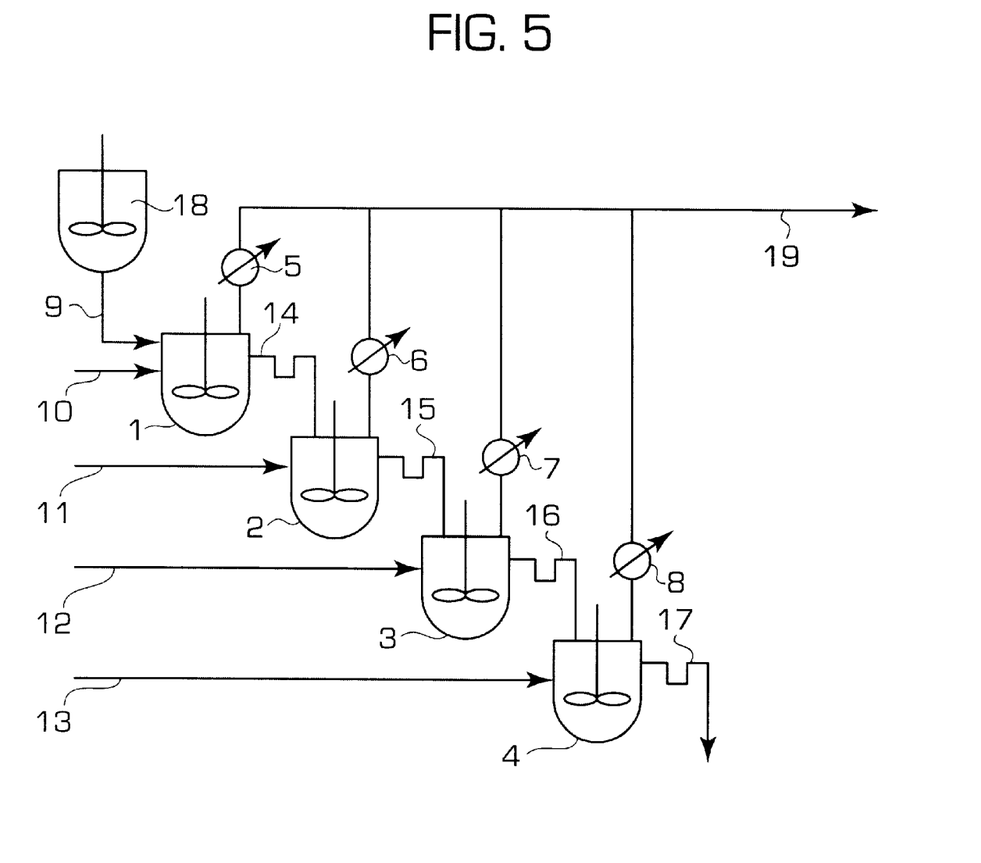
FIG. 5 is a flow sheet of vessel type continuous reactor in the present invention.

The reaction was performed using four stages continuous reactor shown in FIG. 5. As reactors 1, 2, 3 and 4, stirring vessels of capacity 1 L, provided with a baffle plate and a stirrer, which are identical to each other, were used. Raw materials, catalyst and solvent were added to preliminary mixing vessel 18 in the proportion of 1 mol of butanol, 0.037 mol of dibutyltin dibutoxide and 4 mol of diphenyl ether to 1 mol of urea and uniformly dispersed. Then, the mixture thus obtained was continuously introduced into reactor 1 via conduit pipe 9. The introducing velocity was adjusted so as to be 500 g/hr. Butanol was automatically introduced into each reactors 1, 2, 3 and 4 via conduit pipes 10, 11, 12 and 13 so as to maintain reaction temperature of each reactors to a specified temperature. The temperature in each reactors 1, 2, 3 and 4 was set to 170° C. in reactor 1, 185° C. in reactor 2, 195° C. in reactor 3 and 200° C. in reactor 4, respectively. Heating of each reactors was performed with an oil bath attached to each reactors. The amount of butanol to be introduced via conduit pipes 10, 11, 12 and 13 was 28 g/hr in reactor 1, 6 g/hr in reactor 2, 4 g/hr in reactor 3 and 3.5 g/hr in reactor 4. Water of 60° C. was passed through reflux condensers 5, 6, 7 and 8. The amount of liquid was adjusted so as to maintain a constant amount by reaction liquid withdrawing pipes 14, 15, 16 and 17 attached to each reactor. Further, a portion of the reaction liquid withdrawing pipe was bent to make a liquid sealing place so that vapor generated from the reaction liquid may not go to neighboring reactor. Ammonia generated from each reactor was separated from n-butanol through reflux condensers 5, 6, 7 and 8 and then exhausted via conduit pipe 19.

A preliminary mixing vessel 18 and a storage vessel of butanol to be fed via conduit pipes 10, 11, 12 and 13 were kept under dried nitrogen atmosphere. Thus, continuous reaction was performed in each reactor. The component of the reaction liquid obtained via reaction liquid withdrawing pipe 17 was stabilized after 16 hours from starting of the reaction. After 16 hours of the reaction the reaction liquid was analyzed by gas chromatography. The yield of dibutyl carbonate was 60%; the yield of butyl carbamate 38%; non-detected 2%, based on urea. At this time, water content was measured by Karl Fisher's water meter. The water content in the feeding liquid from preliminary mixing vessel 18 was 214 ppm and the water content in butanol in the storage vessel was 283 ppm. The proportion of water in the charge liquid to urea used as the raw material was 1.1 mol %.

COMPARATIVE EXAMPLE 2

The continuous reaction was performed in the same manner as in Example 6 except that preliminary mixing vessel 18 and the storage vessel of butanol were contacted the atmosphere without keeping dried nitrogen atmosphere. After 16 hours of the reaction, the reaction liquid was analyzed by gas chromatography. The yield of dibutyl carbonate was 56%; the yield of butyl carbamate 37%; non-detected 7%, based on urea. At this time, water content was measured by Karl Fisher's water meter. The water content in the feeding liquid from preliminary mixing vessel 18 was 812 ppm and the water content in butanol in the storage vessel was 3893 ppm. The proportion of water in the charge liquid to urea used as the taw material was 5.2 mol %.

COMPARATIVE EXAMPLE 3

The continuous reaction was performed in the same manner as in Example 6 except that dibutyltin oxide was used instead of dibutyltin dibutoxide as the catalyst. After 16 hours of the reaction, the reaction liquid was analyzed by gas chromatography. The yield of dibutyl carbonate was 52%; the yield of butyl carbamate 37%; non-detected 11%.

EXAMPLE 7

Butanol, butyl carbamate and dibutyl carbonate was distilled out together with diphenyl ether under a reduced pressure from the reaction liquid of Comparative Example 3, whereby a distillation residue liquid containing recycling catalyst and diphenyl ether was obtained. Butyl carbamate, urea, butanol, the distillation residue liquid and diphenyl ether which were recovered from the reaction liquid in Comparative Example 3 were added into preliminary mixing 18 so as to maintain molar ratio of butyl carbamate:urea:butanol:recycling catalyst:diphenyl ether to 0.2:0.8:1:0.037:4 and then the continuous reaction was performed in the same manner as in Example 6. After 16 hours from starting of the reaction, the component of the reaction liquid was stabilized. At this time, the reaction liquid was analyzed by gas chromatography. The yield of dibutyl carbonate was 61%; the yield of butyl carbamate 37% non-detected 2%, based on both urea and butyl carbamate. At this time, water content was measured by Karl Fisher's water meter. The water content in the feeding liquid from preliminary mixing vessel 18 was 230 ppm and the water content in butanol in the storage vessel was 330 ppm. The proportion of water in the charge liquid to urea and butyl carbamate used as the raw materials was 1.5 mol %.

According to the process of the present invention, by-production of ammonium carbamate is reduced and dialkyl carbonate can be produced in a high selectivity.

What is claimed is:

1. A process for separation of dialkyl carbonate and alkyl carbamate which comprises:
    adding an aromatic hydroxy compound to a liquid comprising alkyl carbamate represented by the following general formula (1) and dialkyl carbonate represented by the following general formula (2) to obtain a mixed liquid, and
    distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column;

(1)

(2)

wherein R is an alkyl group having 3 to 6 carbon atoms.

2. A process according to claim 1, wherein said process comprises adding said aromatic hydroxy compound is present in an amount of 0.1 to 10 times by mole to said dialkyl carbonate.

3. A process according to claim 1, wherein said aromatic hydroxy compound is phenol, cresol, xylenol or an isomer thereof.

4. A process according to claim 1, wherein said distilling is under a reduced pressure so as to maintain a distillation column top section temperature of 160° C. or below.

5. A process according to claim 1, wherein said dialkyl carbonate is dibutyl carbonate and said aromatic hydroxy compound is phenol.

6. A process according to claim 1, wherein said process comprises further distilling the mixture comprising the aromatic hydroxy compound and the dialkyl carbonate, thereby separating the dialkyl carbonate from the mixture or said process comprises using said mixture comprising the aromatic hydroxy compound and the dialkyl carbonate as raw material for production of alkyl aryl carbonate represented by the following general formula (3) and diaryl carbonate represented by the following general formula (4), (3)

(4)

wherein R is an alkyl group having 3 to 6 carbon atoms and Ar is an unsubstituted phenyl group or a phenyl group only substituted by an alkyl group, an alkoxy group, an aryl group, an aryloxy group or a halogen atom.

7. A process for separation of dialkyl carbonate and alkyl carbamate which comprises:
    separating a catalyst from a reaction mixture produced by reaction of an alkyl alcohol having 3 to 6 carbon atoms with urea, alkyl carbonate or a mixture of urea and alkyl carbonate, said alkyl carbonate being represented by the following general formula (1) in the presence of the catalyst,
    adding an aromatic hydroxy compound to the liquid thus obtained comprising the alkyl carbamate and dialkyl carbonate represented by the following general formula (2) to obtain a mixed liquid,
    distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column;

(1)

(2)

wherein R is an alkyl group having 3 to 6 carbon atoms.

8. A process according to claim 7, wherein said aromatic hydroxy compound is present in an amount of 0.1 to 10 times by mole to said dialkyl carbonate.

9. A process according to claim 7, wherein said catalyst is a halogenide, an inorganic salt, an organic salts an alkoxide or an alkyl alkoxide of at least one metal selected from the group consisting of zinc, lead, copper, tin, titanium, gallium and indium.

10. A process according to claim 7, wherein said catalyst is R'$_2$Sn(OR)$_2$ or R'$_2$SnO in which R' is an alkyl group having 1 to 10 carbon atoms and R is an alkyl group having 3 to 6 carbon atoms.

11. A process according to claim 7, wherein said reaction of an alkyl alcohol having 3 to 6 carbon atoms with urea, alkyl carbamate or mixture of urea and alkyl carbamate is in a high boiling solvent having a boiling point of 180° C. or above.

12. A process according to claim 11, wherein said process comprises feeding said urea, alkyl carbamate or mixture of urea and alkyl carbamate in a state dispersed in said high boiling solvent into a reactor.

13. A process according to claim 11, wherein said high boiling solvent is diphenyl ether.

14. A process according to claim 7, wherein a charge liquid contains water in an amount of 3 mol % or below to total amount of urea, alkyl carbamate or mixture of urea and alkyl carbamate represented by the general formula (1) as raw material.

15. A process according to claim 7, wherein said process comprises further distilling said mixture comprising the aromatic hydroxy compound and the dialkyl carbonate, thereby separating the dialkyl carbonate from the mixture or said process comprises using said mixture comprising the aromatic hydroxy compound and the dialkyl carbonate as raw material for production of alkyl aryl carbonate represented by the following general formula (3) and diaryl carbonate represented by the following general formula (4)

(3)

(4)

wherein R is an alkyl group having 3 to 6 carbon atoms and Ar is an unsubstituted phenyl group or a phenyl group substituted by an alkyl group, an alkoxy group, an aryl group, an aryloxy group or a halogen atom.

16. A process for producing diaryl carbonate which comprises:
   (a) reacting an alkyl alcohol having 3 to 6 carbon atoms with urea, alkyl carbamate or mixture of urea and alkyl carbamate represented by the following general formula (1) in the presence of a catalyst,
   (b) separating the catalyst from a reaction mixture thus produced,
   (c) adding an aromatic hydroxy compound to the liquid thus obtained comprising the alkyl carbamate and dialkyl carbonate represented by the following general formula (2) to obtain a mixed liquid,
   (d) distilling the mixed liquid thus obtained in a distillation column to obtain a mixture comprising the dialkyl carbonate and the aromatic hydroxy compound from a top section of the distillation column and a liquid comprising the alkyl carbamate from a bottom section of the distillation column,
   (e) reacting the mixture comprising the dialkyl carbonate and the aromatic hydroxy compound from a top section of the distillation column, thereby producing alkyl aryl carbonate represented by the following general formula (3) and diaryl carbonate represented by the following general formula (4), and
   (f) producing diaryl carbonate represented by the following general formula (4) by allowing a disproportionation reaction of unreacted alkyl aryl carbonate produced in step (e)

(1)

(2)

(3)

(4)

wherein R is an alkyl group having 3 to 6 carbon atoms and Ar is an unsubstituted phenyl group or a phenyl group substituted by an alkyl group, an alkoxy group, an aryl group, an aryloxy group or a halogen atom.

17. A process according to claim 16, wherein said aromatic hydroxy compound is present in an amount of 1 to 10 times by mole to said dialkyl carbonate.

18. A process according to claim 16, wherein said catalyst in step (a) is a halogenide, an inorganic salt, an organic salt, an alkoxide, an alkyl alkoxide or an alkyl substituted metal oxide of at least one metal selected from the group consisting of zinc, lead, copper, tin, titanium, gallium and indium.

19. A process according to claim 18, wherein said catalyst is $R'_2Sn(OR)_2$ or $R'_2SnO$ in which R' is an alkyl group having 1 to 10 carbon atoms and R is an alkyl group having 3 to 6 carbon atoms.

20. A process according to claim 16, wherein said reaction of an alkyl alcohol having 3 to 6 carbon atoms with urea, alkyl carbamate or mixture of urea and alkyl carbamate is performed in a high boiling solvent having a boiling point of 180° C. or above.

21. A process according to claim 20, wherein said process comprises feeding said urea, alkyl carbamate or mixture of urea and alkyl carbamate in a state dispersed in said high boiling solvent into a reactor.

22. A process according to claim 20, wherein said high boiling solvent is diphenyl ether.

23. A process according to claim 16, wherein a charged liquid contains water in an amount of 3 mol % or below to total amount of urea, alkyl carbamate or mixture of urea and alkyl carbamate as raw material.

24. A process according to claim 16, wherein the catalyst present in steps (e) and (f) is an oxide, an alkoxide, an aryloxide or an alkyl substituted oxide of a metal selected from the group consisting of tin and titanium or a mixture containing at least one member selected from said compounds.

* * * * *